United States Patent [19]

Onaka et al.

[11] Patent Number: 5,122,300
[45] Date of Patent: Jun. 16, 1992

[54] METHOD FOR PREVENTING AGGLOMERATION OF POWDER

[75] Inventors: Tadao Onaka; Akihiko Nomura, both of Shinnanyo; Hiroshi Fukuda, Tokuyama; Shoji Arai, Tokuyama, all of Japan

[73] Assignee: Tosoh Corporation, Shinnanyo, Japan

[21] Appl. No.: 773,433

[22] Filed: Oct. 9, 1991

[30] Foreign Application Priority Data

Oct. 12, 1990 [JP] Japan .................................. 2-272272

[51] Int. Cl.$^5$ ................................................ C09K 3/00
[52] U.S. Cl. ..................................... 252/384; 252/383
[58] Field of Search ................................ 252/383, 384

[56] References Cited

U.S. PATENT DOCUMENTS 4,670,181  6/1987  Mollinger et al. ............. 252/186.25

Primary Examiner—Deborah L. Kyle
Assistant Examiner—Valerie D. Fee
Attorney, Agent, or Firm—Oblon, Spivak, McClelland, Maier & Neustadt

[57] ABSTRACT

A method for preventing agglomeration of powder, characterized in that a poly(oxyethylene)diglycosic acid is incorporated as an anti-agglomeration agent to the powder.

5 Claims, No Drawings

METHOD FOR PREVENTING AGGLOMERATION OF POWDER

The present invention relates to a method for preventing agglomeration of powder which is likely to agglomerate. More particularly, it relates to a method for preventing agglomeration of powder by using a poly(oxyethylene)diglycosic acid as an anti-agglomeration agent.

A powder of an amine such as piperazine or triethylenediamine (hereinafter referred to simply as TEDA) is a compound which usually has coherence and adherence and thus is likely to agglomerate. Not to mention such a specific powder, a highly hygroscopic powder or a highly sublimable powder in general usually readily undergoes agglomeration due to an inclusion of a small amount of moisture or due to an increase of the temperature. Therefore, such an agglomerative powder is required to be handled with due care, and once such a powder has agglomerated, the handling tends to be extremely difficult. As measures to prevent agglomeration of such an agglomerative powder, it is common to employ a method of removing impurities contained in the powder and enlarging the particle size of the powder itself, a method of adding an anti-agglomeration agent to the powder or a method of storing the powder by means of a closed vessel. However, among agglomerative powders, there is one which undergoes agglomeration even when stored in a closed vessel, such as piperazine, or a highly sublimable substance such as TEDA which tends more likely to agglomerate when so stored. Therefore, there has been no appropriate method for preventing agglomeration of such a powder. Further, such a powder has very strong agglomerating nature, and it is usually difficult to prevent the agglomeration by enlarging the particle size. As a method for preventing agglomeration of such a highly agglomerative powder, it is usually believed to be effective to incorporate a suitable anti-agglomeration agent.

For the selection of such an anti-agglomeration agent, it is desired to select an agent which is capable of effectively accomplishing the object in an amount as small as possible and which does not impart an odor or a color to the powder by the addition. Further, it is desired to select an anti-agglomeration agent which presents no adverse effects to the physical properties of the powder in connection with the purpose of the powder and which is inexpensive. As conventional anti-agglomeration agents, silica powder (Japanese Unexamined Patent Publication No. 203039/1982) and polyethylene glycols (Japanese Examined Patent Publication No. 46758/1988) are known. However, the silica powder is effective only to temporarily avoid the contact of crystals to one another and its anti-agglomerating action is not so strong for a long term. On the other hand, liquid anti-agglomeration agents such as polyethylene glycols may simply be mixed with TEDA powder. As a consequence, however, the TEDA powder tends to be wet, and in a long range storage, the liquid tends to flow to the bottom of the container and tends to be non-uniform in the container, whereby the anti-agglomerating action tends to be low.

Whereas, Japanese Examined Patent Publications No. 15 62241/1988 and No. 3142/1989 disclose that by an addition of a TEDA polymer as an additive during a precipitation step, it is possible to simplify the process of the addition so that the process control can be easy, and the TEDA polymer exhibits a high level of anti-agglomerating action, whereby adequate effects can be obtained by an addition of a very small amount of the polymer. However, this TEDA polymer is insoluble in most organic solvents.

Powders usually have coherence and adherence in many cases. It is common to employ an operation such as granulation or classification to reduce such nature. However, in a case of a agglomerative powder such as a highly sublimable powder of e.g. TEDA, sublimation and condensation are repeated due to a change of e.g. the external temperature, whereby a strong bridge will be formed between powder particles (crystals). Thus, TEDA tends to agglomerate entirely in the container and tends to be hardly disintegrated.

TEDA is usually synthesized or produced from e.g. N-aminoethylpiperazine or hydroxyethylpiperazine. By such a method, TEDA is obtainable as slightly yellow white crystals. As a by-product, an alkylpiperazine or the like is contained. This by-product has an anti-agglomerating action to some extent. However, TEDA crystals of high purity have been desired in recent years, and consequently, TEDA crystals having a purity of at least 99.9% are now produced as a result of an improvement in the purification technique. Accordingly, the agglomerating nature of TEDA has been thereby sharply increased, and there has been a problem from the viewpoint of the production process or the storage.

It is an object of the present invention to provide a method for preventing agglomeration of powder having agglomerating nature, whereby prevention of agglomeration can effectively be conducted by adding a small amount of an anti-agglomeration agent which is excellent in the solubility to various solvents and which is inexpensive and has no adverse effect to the physical properties of the powder, as compared with the conventional methods.

As a result of an extensive study in view of the above-mentioned circumstances, the present inventors have found it possible to effectively control agglomeration of powder by using a poly(oxyethylene)diglycosic acid as an anti-agglomeration agent, and have arrived at the present invention on the basis of this discovery.

Thus, the present invention provides a method for preventing agglomeration of agglomerative powder, which comprises incorporating to the powder a poly(oxyethylene)diglycosic acid as an anti-agglomeration agent.

Now, the present invention will be described in detail with reference to the preferred embodiments.

In the present invention, the agglomerative powder means a highly hygroscopic and/or sublimable powder of e.g. piperazine, TEDA, ammonium sulfate, ammonium chloride or sodium chloride.

Two types of causes are conceivable as the main causes for agglomeration of powder i.e. agglomeration due to absorption of moisture and agglomeration due to bridging of powder particles (crystals) by sublimation and condensation. The former can be avoided by packaging. Otherwise it can be avoided by improving the quality control of the product. With respect to the latter, there has been no effective method discovered which presents no adverse effects to the physical properties of the powder and which fully satisfies other conditions. The present invention presents a very effective agglomeration-preventing method by incorporating an anti-agglomeration agent which prevents absorption of moisture and the sublimation and condensation action.

The mechanism for preventing agglomeration in the present invention is considered to be as follows. Poly(oxyethylene)diglycosic acid exhibits excellent solubility to various solvents. A solution of such poly(oxyethylene)diglycosic acid in water or in an organic solvent is mixed to the powder, followed by drying to form a film of poly(oxyethylene)diglycosic acid on the surface of the powder and thereby to microcapsulate the crystals, so that the contact of the crystal-forming component with outer atmosphere or the contact of crystals to one another is prevented, whereby the absorption of moisture and the sublimation and condensation, are suppressed. Thus, agglomeration of crystals to one another is suppressed, and agglomeration-preventing effects can be obtained.

The poly(oxyethylene)diglycosic acid in the present invention is a compound of the following formula (1):

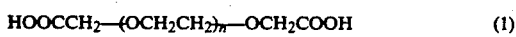

$$HOOCCH_2\text{---}(OCH_2CH_2)_n\text{---}OCH_2COOH \qquad (1)$$

wherein n is an integer of at least 1.

The poly(oxyethylene)diglycosic acid is commercially available under a trade name "PEO acid" from Kawaken Fine Chemicals K.K. This poly(oxyethylene)diglycosic acid is marketed in three types of #400, #1000 and #4000 depending upon the average molecular weight.

In the present invention, there is no particular restriction as to the average molecular weight of the poly(oxyethylene)diglycosic acid. The one having a low molecular weight is a highly viscose liquid, and its high molecular weight product is solid. Therefore, a solvent is required for the incorporation of the poly(oxyethylene)diglycosic acid. However, a poly(oxyethylene)diglycosic acid having a high molecular weight which becomes solid in the drying step after the incorporation or in the state of the final product, is preferred.

According to the present invention, the amount of the poly(oxyethylene)diglycosic acid incorporated to the powder is usually from 0.1 to 2%, preferably from 0.5 to 1%. Further, in the present invention, there is no particular restriction as to the method for incorporation. For example, it is common to employ a method wherein after the preparation of powder, the powder and a solution of the poly(oxyethylene)diglycosic acid in water or in an organic solvent are thoroughly mixed by means of a mixing apparatus such as a ribbon blender or a V-type mixer. However, to employ such a mixing apparatus, the process tends to be complex, and the cost is expected to be substantial. Whereas, if a solution of the poly(oxyethylene)diglycosic acid in water or in an organic solvent is sprayed or otherwise added during the liquid removal step immediately after precipitation i.e. to a TEDA crystal cake in a centrifugal separator, followed by drying, it is possible to effectively and uniformly accomplish the coating on the TEDA crystal surface without requiring any mixing apparatus. Otherwise, it may be added during the precipitation step, as disclosed in Japanese Examined Patent Publication No. 62241/1988.

The poly(oxyethylene)diglycosic acid has an appearance of a colorless, transparent liquid to a white paraffinic solid and is chemically very stable. Therefore, it does not adversely affect the physical properties of the powder, and it shows excellent solubility to various solvents and thus has excellent properties as an additive or coating agent.

As described in the foregoing, the present invention provides an epoch-making agglomeration-preventing technique in which a very small amount of a water-soluble poly(oxyethylene)diglycosic acid is added to powder to coat it on the powder surface to impart excellent agglomeration-preventing effects by suppressing moisture absorption and sublimation of the powder and preventing the contact of the powder particles to one another.

Now, the present invention will be described in further detail with reference to Examples. However, it should be understood that the present invention is by no means restricted by such specific Examples.

EXAMPLE 1

Into a 5l flow-type mixer, 1 kg of TEDA powder and 10 g of poly(oxyethylene)diglycosic acid #4000 (PEO acid, manufactured by Kawaken Fine Chemical K.K.) as an anti-agglomeration agent, dissolved in 50 ml of methanol, were introduced and mixed. The mixture was dried by a vacuum dryer to obtain a sample.

The measurement of the agglomeration degree and the evaluation standards were as follows. Namely, the obtained sample was packed in a container having a size of 5 cm×5 cm and a height of 2 cm, and a plastic plate of 5 cm×5 cm was placed thereon. A weight of 300 g was placed thereon, and the container was stored in a desiccater having a humidity of not higher than 1%. During the storage, the pressure exerted to the crystals was 12 g/cm². After the storage in the desiccater for one month, the weight and the container were removed, and a pressure was exerted to the center portion of the crystal block with the plastic plate located beneath, by a Kiya-type hardness meter, whereby the pressure at breakage was read. The values thus obtained were classified into the following three rankings, which were used as indices for evaluation of the agglomeration degree.

A rank: Crystal block which can readily be broken with a slight impact with a breaking pressure of not higher than 1.0 kg/cm² and in which no substantial progress of agglomeration was observed.

B rank: Crystal block with a breaking pressure of not higher than 10.0 kg/cm² which can not be broken by a low level of impact and in which agglomeration was found progressed entirely.

C rank: Crystal block which requires a considerably strong impact for breakage with a breaking pressure of at least 10.0 kg/cm² and in which agglomeration was found completely progressed.

The result belonged to A rank. Thus, the anti-agglomeration agent was found to have excellent anti-agglomerating effects. Further, the powder was in a dry state, and when it was dissolved in a solvent such as dipropylene glycol, no insoluble matter was observed.

COMPARATIVE EXAMPLE 1

The agglomeration degree was measured in the same manner as in Example 1 using TEDA containing no anti-agglomeration agent. The result belonged to C rank, and agglomeration was found to have progressed substantially.

COMPARATIVE EXAMPLE 2

1 kg of TEDA and 2 g of silica gel (manufactured by Nippon Silica Gel Kogyo K.K., bulk density: 40 g/l, average particle size: 2 μm) were thoroughly mixed by a V-mixer, and the obtained mixture was used as a sample. Otherwise, the operation was conducted in the same manner as in Example 1. The result belonged to B rank, and a certain degree of agglomeration was observed.

COMPARATIVE EXAMPLE 3

The operation was conducted in the same manner as in Example 1 except that solventless polyethylene glycol #200 (manufactured by Kanto Kagaku) was used instead of the poly(oxyethylene)diglycosic acid as the anti-agglomeration agent. The agglomeration degree of the product was measured and found to be B rank. Further, the powder was in a wet state.

COMPARATIVE EXAMPLE 4

3,000 ml of a TEDA methanol solution having a composition comprising 50 parts by weight of TEDA and 50 parts by weight of methanol, was introduced into a flask having an internal capacity of 5,000 ml, and 0.15 g of TEDA polymer (ethylene-piperazine copolymer) prepared by the synthesis disclosed in Japanese Unexamined Patent Publication No. 62241/1988), was added thereto. The mixture was subjected to methanol removal by an evaporator, whereby 1,100 ml of methanol was distilled. The residual liquid was left to stand still at a room temperature and then cooled to a liquid temperature of 20° C. Precipitated TEDA crystals were collected by filtration under suction with a filer paper of No. 5C and then dried under vacuum to obtain 450 g of TEDA crystals. The TEDA polymer contained in the TEDA crystals was 0.05 g (111 ppm). With respect to this sample, the agglomeration degree was evaluated in the same manner as in Example 1.

The result belonged to A rank, and excellent agglomeration-preventing effects were exhibited, but when dissolved in dipropylene glycol solution, a certain level of turbidity was observed.

EXAMPLE 2

The operation was conducted in the same manner as in Example 1 except that poly(oxyethylene)diglycosic acid #1000 was used instead of #4000 as the anti-agglomeration agent. As a result, the agglomeration degree was A rank.

EXAMPLE 3

The operation was conducted in the same manner as in Example 1 except that poly(oxyethylene)diglycosic acid #400 was used instead of #4000 as the anti-agglomeration agent. As a result, the agglomeration degree was A rank.

EXAMPLE 4

The operation was conducted in the same manner as in Example 1 except that ammonium chloride was used instead of the TEDA powder as a agglomerative powder. The agglomeration degree of the product was evaluated. As a result, the agglomeration degree was A rank.

COMPARATIVE EXAMPLE 5

The operation was conducted in the same manner as in Example 4 except that no poly(oxyethylene)diglycosic acid was added. As a result, agglomeration of ammonium chloride was found progressed to the interior, and the agglomeration degree was C rank.

EXAMPLE 5

The operation was conducted in the same manner as in Example 1 except that ammonium sulfate was used instead of the TEDA powder as an agglomerative powder. The agglomeration degree of the product was evaluated. As a result, the agglomeration degree was A rank.

COMPARATIVE EXAMPLE 6

The operation was conducted in the same manner as in Example 5 except that no poly(oxyethylene)diglycosic acid was added. As a result, agglomeration of ammonium sulfate was found progressed to the interior, and the agglomeration degree was C rank.

We claim:

1. A method for preventing agglomeration of powder, characterized in that a poly(oxyethylene)diglycosic acid is incorporated as an anti-agglomeration agent to the powder.

2. The method according to claim 1, wherein said powder is a highly hygroscopic or sublimable powder of piperazine, triethylenediamine, ammonium sulfate, ammonium chloride or sodium chloride.

3. The method according to claim 1, wherein the poly(oxyethylene)diglycosic acid is a compound of the formula:

$$HOOCH_2-(OCH_2CH_2)_nOCH_2COOH \quad (1)$$

wherein n is an integer of at least 1,.

4. The method according to claim 1, wherein the poly(oxyethylene)diglycosic acid is incorporated in an amount of from 0.1 to 2% by weight to the powder.

5. The method according to claim 1, wherein the poly(oxyethylene)diglycosic acid is incorporated in an amount of from 0.5 to 1% by weight to the powder.

* * * * *